United States Patent
González Palomo et al.

(10) Patent No.: US 9,790,279 B2
(45) Date of Patent: Oct. 17, 2017

(54) PHARMACEUTICAL COMPOSITIONS FOR THE TREATMENT OF TUMORS EXPRESSING EGFR AND GM3 N-GLYCOLYL GANGLIOSIDE (NEUGCGM3)

(71) Applicant: Centro De Immunologia Molecular, La Habana (CU)

(72) Inventors: Adys González Palomo, La Habana (CU); Adriana Carr Perez, La Habana (CU); Kalet León Monzón, La Habana (CU); Rancés Blanco Santana, La Habana (CU); María del Carmen Barroso Alvarez, La Habana (CU); Amparo Emilia Macías Abraham, La Habana (CU); José Enrique Montero Casimiro, La Habana (CU)

(73) Assignee: CENTRO DE IMMUNOLOGIA MOLECULAR, La Habana (CU)

( * ) Notice: Subject to any disclaimer, the term of this patent is extended or adjusted under 35 U.S.C. 154(b) by 0 days.

(21) Appl. No.: 14/369,435

(22) PCT Filed: Dec. 4, 2012

(86) PCT No.: PCT/CU2012/000007
§ 371 (c)(1),
(2) Date: Jun. 27, 2014

(87) PCT Pub. No.: WO2013/097834
PCT Pub. Date: Jul. 4, 2013

(65) Prior Publication Data
US 2014/0363494 A1    Dec. 11, 2014

(30) Foreign Application Priority Data

Dec. 27, 2011 (CU) .................... 2011/0245

(51) Int. Cl.
| | | |
|---|---|---|
| *A61K 39/395* | (2006.01) | |
| *C07K 16/28* | (2006.01) | |
| *A61K 39/00* | (2006.01) | |
| *C07K 16/42* | (2006.01) | |
| *C07K 16/30* | (2006.01) | |

(52) U.S. Cl.
CPC ...... *C07K 16/2863* (2013.01); *A61K 39/0011* (2013.01); *A61K 39/3955* (2013.01); *A61K 39/39558* (2013.01); *C07K 16/3084* (2013.01); *C07K 16/4266* (2013.01); *A61K 2039/505* (2013.01); *A61K 2039/507* (2013.01); *A61K 2039/545* (2013.01); *C07K 2317/24* (2013.01); *C07K 2317/76* (2013.01)

(58) Field of Classification Search
None
See application file for complete search history.

(56) References Cited

FOREIGN PATENT DOCUMENTS

| | | |
|---|---|---|
| EP | 0 586 002 A2 | 3/1994 |
| EP | 1 798 243 A2 | 6/2007 |

OTHER PUBLICATIONS

Estevez et al. (2000) Vaccine 18: 190-197.*
Hanai N et al: HA novel ganglioside, de-N-acetyl-GM3 (II3NeuNH2LacCer), acting as a strong promoter for epidermal growth factor receptor kinase and as a stimulator for cell growth., The Journal of Biological Chemistry May 5, 1988, vol. 263, No. 13, May 5, 1988, pp. 6296-6301, XP002691997, ISSN: 0021-9258 the whole document.
Weis F M et al: "Regulation of epidermal growth factor receptor signal transduction. Role of gangliosides", The Journal of Biological Chemistry Jul. 15, 1990, vol. 265, No. 20, Jul. 15, 1990 (Jul. 15, 1990), pp. 12059-12066, XP002691996, ISSN: 0021-9258 the whole document.

* cited by examiner

Primary Examiner — Michael Pak
(74) Attorney, Agent, or Firm — Rothwell, Figg, Ernst & Manbeck, P.C.

(57) ABSTRACT

The present invention relates to pharmaceutical compositions for the treatment of malignant tumors. Particularly those tumors that express EGFR and GM3 N-glycolyl ganglioside targets to enhance the therapeutic effect produced by separated therapies against these targets. The pharmaceutical compositions of the invention include antibodies and/or vaccines against each of the targets. Additionally the present invention relates to methods for applying the compositions of the invention.

18 Claims, 3 Drawing Sheets

PHARMACEUTICAL COMPOSITIONS FOR THE TREATMENT OF TUMORS EXPRESSING EGFR AND GM3 N-GLYCOLYL GANGLIOSIDE (NEUGCGM3)

CROSS REFERENCE TO RELATED APPLICATION

This application is a 35 U.S.C. 371 National Phase Entry Application from PCT/CU2012/000007, filed Dec. 4, 2012, which claims the benefit of Cuban Patent Application No. CU/P/2011/0245 filed on Dec. 27, 2011, the disclosures of which are incorporated herein in their entirety by reference.

TECHNICAL FIELD

This invention relates to the field of human medicine, particularly to the treatment of tumors that overexpress EGFR and N-glycolyl ganglioside (NeuGcGM3).

PREVIOUS ART

Epidermal growth factor receptor (EGFR) is one of the molecular targets most used in current clinical evaluation. This molecule is overexpressed in a variety of human epithelial tissues (Yarden, Y., and Sliwkowski M. X., Nat. Rev. Mol. Cell Biol. 2001, 2: 127-137). Two treatments are most often used in therapies to inhibit the function of EGF receptor: neutralization of monoclonal antibodies (MAbs) and the small molecules that inhibit tyrosine kinase activity (TKI, tyrosine quinasa inhibitor) (Ciardiello, F., and Tortora G., N. Engl. J. Med. 2008, 358: 1160-1174). Although it also has been demonstrated that a vaccine with the extracellular domain of EGFR when using the very small size particle (VSSP) as adjuvant generated an anti-metastatic effect in the murine model of Lewis lung carcinoma (Sánchez Ramírez B., et al, Int. J. Cancer. 2006, 119: 2190-2199). Treatment with anti-EGFR monoclonal antibodies mediate tumor regression by the interruption of oncogenic signals and the induction of an innate immune response mechanism mediated by the Fc receptor (Martinelli, E., et al, Clin. Exp. Immunol. 2009, 158: 1-9).

Several human monoclonal antibodies against EGFR have been generated including: Cetuximab (Garrett C R, and Eng C., Expert Opin Biol Ther. 2011; 11: 7, 937-49) and Nimotuzumab (Mateo C, Immunotechnology 1997; 3:71-81). The antitumor effect of Nimotuzumab in the therapy of different tumors that overexpress the EGFR has been described (Crombet T, et al, Cancer Biol Therapy. 2006, 5:375-379) or in combination with other therapies (Crombet T, et al, J Clin Oncol. 2004, 22:1646-1654; Zhao K L, et al, Invest New Drugs. 2011 Pre published online September 8). On the other hand, the 7A7 MAb generated against murine EGFR demonstrated antitumor effect mediated by T cells in the treatment of Lewis lung carcinoma (Garrido G., et al, Cancer Immunol Immunother. 2007, 56: 1701-1710).

Another of the most studied targets is gangliosides, which are glycosphingolipids that contain sialic acid in their structure. These molecules are present in normal tissues and over-expressed in tumor tissues (Zhang S, et al. Int J Cancer 73:42-49, 1997). There are two forms of sialic acid: N-acetylated and N-glycolylated, the latter described in human tumors (Malykh Y N., et al, Biochimie. 2001, 83:7 623-634), both as gangliosides (Kawai T. et al, 1991 Cancer. Res. (51) 1242-1246) and N-glycolylated glycoproteins (Devine P. L., et al, Cancer Research, 1991, 51: 21, 5826-5836). For this reason these molecules have been identified in many malignant tumors making them attractive targets for cancer therapy. Particularly, NeuGcGM3 ganglioside is specifically recognized by 14F7 MAb (Carr A. et al, Hybridoma, 2000, 19: 3, 241-247). This ganglioside has been identified in different tumors by various methods (Blanco R., et al, ISRN Pathology. 2011, Article ID 953803, 10 pag., Marquina et al, Cancer Research. 1996, 56: 22, 5165-5171)

Active immunotherapy against NeuGcGM3 in tumors has been published using NeuGcGM3/VSSP molecular vaccine (Estevez F., et al, Vaccine. 1999, 18:190-197) which has demonstrated its immunogenicity and its safety in advanced breast cancer patients (Carr A., et al, JCO. 2003, 21:1015-1021). Furthermore, it has been demonstrated in the preclinical stage that its potent antitumor effect (anti-metastatic), is mediated by a mechanism of cellular response of NK and CD8+ cells (Labrada M., et al, Expert Opin. Biol. Ther. 2010, 10:2, 153-162). At the same time, an anti-tumor effect has been generated in patients with non small cell lung cancer immunized with the anti-idiotypic vaccine (1E10 anti-idiotypic monoclonal antibody, Racotumumab, which mimics N-glycolylated gangliosides (Alfonso S., et al, Cancer Biology & Therapy. 2007, 6:12, 1847-1852). Published results with this vaccine show its immunogenicity and safety (Alfonso M., et al, Journal of Immunology. 2002, 168: 2523-2529).

The EGFR in membrane microdomains plays an essential role in controlling the growth of tumor cells. It has been demonstrated that GM3 ganglioside inhibits EGFR-dependent proliferation in a great variety of cell lines, both in vivo and in vitro. GM3 inhibits EGFR kinase activity (EGFR autophosphorylation). GM3 ganglioside inhibits the autophosphorylation of the kinase domain of EGFR. GM3 has the potential capacity of allosterically regulate structural transition of the inactive form to signaling by the EGFR dimer in order to prevent the autophosphorylation of the kinase intracellular domain to the ligand binding site (Coskun Ü., et al, PNAS. 2011, 108: 22, 9044-9048). Changes in the composition of gangliosides in the membrane are important in the regulation of the EGFR signal transduction (Zurita A R., et al, Biochem. J. 2001, 35: 465-472). Promising results are expected in the medical practice of simultaneous or alternate anti-tumor therapies (Takeda K. et al, Cancer Sci., 2007; 98: 9, 1297-1302). But not all schemes of applying anti-tumor therapies give positive and synergistic results in practice. In a Phase III clinical study in metastatic colorectal cancer, where the anti-EGFR MAb (Cetuximab) and anti-vascular endothelial growth factor MAb (Bevacizumab) were used, together with a potent chemotherapeutic drug regimen there was a worsening of the evolution of cancer, which also caused serious adverse events as compared with patients who received Bevacizumab plus chemotherapy only (Tol J., et al, N Engl J Med. 2009; 360:6, 563-72). The successful implementation of various therapies in a patient is the result of the specific functional relationships between selected targets for these therapies, tumor localization, as well as the nature of the therapies applied in each case (antibodies, vaccines or others).

Today there is evidence in the literature of a structural and functional relationship between gangliosides and EGFR in tumor cells. However, the practical implication of this relationship in the successful application in the same patient of therapies against EGFR and gangliosides targets has not been addressed either in clinical or preclinical studies. The novelty of the present invention lies in the preclinical and clinical demonstration for the first time of the synergistic potentiation of the antitumor activity derived from applying anti-EGFR therapies and anti-NeuGcGM3 vaccines, in tumors co-expressing these targets.

DESCRIPTION OF THE INVENTION

The present invention relates to pharmaceutical cancer compositions aimed specifically at EGFR and GM3 N-glycolyl ganglioside targets with the purpose of enhancing the therapeutic effect produced by therapies against those targets separately. In one embodiment, the invention comprises vaccines which target GM3 N glycolyl and antibodies against EGFR. In another embodiment, the invention comprises vaccines which target N glycolyl GM3 and vaccines which target the EGFR.

In other embodiments of the invention, the vaccine against the ganglioside target comprises vaccines such as: NeuGcGM3/VSSP vaccine and/or anti-idiotype vaccine (Racotumumab MAb adjuvated in alumina). In another embodiment the invention comprises anti-EGFR therapies such as Nimotuzumab MAb and/or EGFR vaccine.

In another embodiment the invention encompasses a composition comprising a compound against EGF receptor and a compound against the NeuGcGM3 ganglioside for use in cancer treatment.

In another aspect, the invention provides a pharmaceutical composition that comprises any of the compounds described above, mixed with a pharmaceutically acceptable excipient.

The compounds of the invention are useful as medicaments, and are useful for the manufacture of medicaments, including medicaments for the treatment of conditions such as cancer.

In another embodiment the therapeutic compositions of the present invention are useful in cancer treatment, particularly in human tumors of different localizations. Preferably the therapeutic compositions of the present invention are used for treatment of those tumors that express simultaneously EGFR and the N-glycolylated variant of gangliosides. Most preferably used to treat lung, breast, digestive system, urogenital system and sarcoma tumors derived of neuroectodermic tissue and lymphoproliferative disorders.

Any suitable formulation of a compound described above may be prepared for administration by methods known in the art. The selection of useful excipients or carriers can be achieved without undue experimentation, based on the intended route of administration and the physical properties of the compound being administered.

Any suitable route of administration may be used, according to the doctor treating the patient criterion, including but not limited to: parenteral, intravenous, intramuscular, transdermal, topical and subcutaneous. The preparation of the suitable formulations for each route of administration is known in the art.

Formulation of each substance often includes a diluent and, in some cases, adjuvants, buffers, preservatives, etc. These compounds may also be administered in liposomes or microemulsions compositions.

For injection, formulations can be prepared in conventional forms such as: liquid solutions or suspensions or solid forms suitable for the solution or suspension in liquid prior to injection. Suitable excipients include, for example: water, saline, dextrose and similar compounds.

The compounds of the invention may be used alone or in combination with another therapeutic agent. In particular embodiments the invention refers to the combination with conventional chemotherapy and/or radiation used for the type of tumor being treated.

In another embodiment the present invention also relates to the simultaneous, staggered or alternate use of therapies directed against EGFR and GM3 N-glycolyl ganglioside targets in cancer treatment.

The compound against EGFR and the compound/s against GM3 N-glycolyl ganglioside target are administered separately, even at different times and with different frequencies. Both compounds may be administered by any known route, such as: subcutaneous, intravenous, intradermal, intramuscular or intraperitoneal, and the like. In many embodiments, at least one and optionally two therapeutic agents can be administered parenterally.

When a compound or a composition of the invention are used in combination with another anticancer agent, the present invention provides, for example, simultaneous, staggered or alternate treatment. Thus, the compound/s of the invention may be administered simultaneously in separate pharmaceutical compositions, and wherein a compound of the invention can be administered before or after the other anticancer agent with a difference of seconds, minutes, hours, days or weeks.

The present invention provides methods for controlling and/or inhibiting tumor growth, comprising administration of the combination of the compounds described herein to a subject in need thereof in an amount effective to control or reduce tumor proliferation. In certain embodiments, tumor proliferation is associated to a tumor in different clinical stages, provided that tumors co-express the EGFR and N-glycolyl GM3. In a particular embodiment the present invention relates lung, breast, digestive system, urogenital system and sarcoma tumors derived of neuroectodermic tissue and lymphoproliferative disorders.

The invention also includes methods for treating cancer in a subject in need of such treatments which comprise methods for: administering to the subject a therapeutically effective amount of a compound against EGFR, useful for treating of such disorder and administering to the subject a NeuGcGM3 vaccine or anti-idiotypic vaccine in an amount effective to enhance the desired effect. Improve according to the present invention relates to partial or complete regression or stabilization of the clinical symptoms of the disease. In another embodiment of the present invention improving means decrease tumor size and/or induce an increased survival on the subject.

In a certain embodiment the invention includes a method comprising a first induction phase and a second maintenance phase. In a particular embodiment, the induction phase comprises administering to the patient the anti-EGFR vaccine in a dose in the range of approximately 0.1 to 2 mg, for a time period of approximately 7 to 14 days for approximately 8 to 14 weeks. During that period, patients will be administered NeuGcGM3 anti-ganglioside therapy which comprises a NeuGcGM3 vaccine or an anti-idiotypic vaccine at a dose in the range of approximately 0.1 to 2 mg at intervals of approximately 7 to 14 days.

The invention includes a method comprising administering to the patient passive therapy with anti-EGFR at a dose in the range of approximately 100 to 400 mg during a time interval from approximately 6 to 10 weeks. In another embodiment the anti-EGFR therapy comprises administration of a vaccine against EGFR, in doses ranging from approximately 0.1 to 2 mg at time intervals of approximately 7 to 14 days. During that period, patients will additionally receive the NeuGcGM3 vaccine or an anti-idiotypic vaccine at doses in the range from approximately 0.1 to 2 mg at time intervals of approximately 7 to 14 days.

In another embodiment, the second phase of the invention treatment method comprises a treatment schedule designed to be administered as maintenance therapy while no toxicity and/or clinical symptoms of the disease appear. In the maintenance phase, vaccines are preferably administered at the doses described above and at a time interval of approximately 1 to 3 months. In another embodiment, passive therapies are administered in an interval from approximately 14 days to 3 months. The therapy scheme can be administered in a time period from approximately 1 to 5 years.

In some embodiments, the therapeutic agent directed to EGFR and the NeuGcGM3 vaccine or anti-idiotypic vaccine are administered simultaneously. The therapeutic agent directed to EGFR and NeuGcGM3 vaccine or anti-idiotype vaccine are sometimes used at the same time on the subject.

In some embodiments the NeuGcGM3 anti-ganglioside therapy can be administered by: subcutaneous, intravenous, intradermal, intramuscular or intraperitoneal injections, while the anti-EGFR therapy can be administered by subcutaneous, intravenous, or intramuscular routes. In other embodiments the administration site is determined by the presence of afferent lymph nodes.

In another embodiment, during the application of therapies, certain biochemical and imaging parameters of patients are recorded. Cellular and humoral immunity is preferably analyzed using the blood of patients. Blood tests are performed at a frequency ranging from weekly to every six months.

"Co-expression" as used in the present invention means that both targets are expressed but may or may not have a close structural relationship, the operational criterium for this definition is by determination of EGFR and N-glycolylated ganglioside (NeuGcGM3) expression by double staining, using a fluorescent microscope and a processor that allow the superposition of images.

"Co-localization" as used in the present invention refers to both targets being structurally close, the operational criterium for this determination is by definition of EGFR and N-glycolylated ganglioside (NeuGcGM3) expression by double staining using a confocal microscope.

In a further embodiment the present invention encompasses the use of a compound against EGFR and a compound against NeuGcGM3 ganglioside, for the preparation of a medicament for retarding tumor growth in a patient according to the treatment regimen that involves:
  (a) first administering to the patient the medicament comprising the compound against the EGF receptor and,
  (b) subsequently administering to the same patient the medicament comprising the compound against NeuGcGM3 ganglioside.

Administration can be in this order or in reverse order, that is, first administering to the patient the medicament comprising the compound against NeuGcGM3 ganglioside and subsequently administering to the same patient the medicament comprising the compound against EGF receptor.

In a particular embodiment the present invention encompasses a kit of reagents for therapy of tumors which co-express EGFR and NeuGcGM3 ganglioside targets, said kit comprises the simultaneous, staggered or alternate administration of a compound against EGFR and another compound against NeuGcGM3 ganglioside.

Determination of Co-Expression of EGFR and N-Glycolylated Ganglioside (NeuGcGM3) in Human Tumors of Different Localizations.

Measuring the expression of EGFR and NeuGcGM3 therapeutic targets in tumors can be performed using any of the methods described in the art for such purposes. Such measurement is performed in tumors of different localizations and origin, on tumor samples previously fixed in formol or on fresh tissue slices. In a preferred embodiment, the detection is performed by employing immunological techniques for EGFR and the GM3 N-glycolated variant recognition. Particularly immunohistochemistry and brightfield microscopy can be used separately for immunorecognition of both molecules or immunofluorescence and fluorescence microscopy to determine the co-expression or the immunofluorescence and confocal microscopy to determine the co-localization.

In preferred embodiments of the present invention the EGFR can be detected using ior egf/R3m MAb (5-20 µg/ml), described in the EP 0586002B1 and NeuGcGM3 can be detected using 14F7 MAb (5-25 µg/ml), described in the U.S. Pat. No. 6,429,295 or EP 0972782B1. In one embodiment of the present invention, for immunorecognition by separate of both molecules (Simple staining) Dako, LSAB® Peroxidase System, DAB (Dako, Carpinteria, Calif., USA) can be used as detection system.

Given that the EGFR is located on the cytoplasmic membrane of tumor cells while the GM3 N-glycolyl is located in the membrane and intracytoplasmic, immunorecognition is deemed to be positive when the intensity of the reaction is equal or larger 20% positivity.

In a preferred embodiment, the co-expression of both molecules can be detected using a double staining technique and analyzed by fluorescence microscopy, only in those tumor samples where immunorecognition was previously positive for both molecules separately. While the co-localization of both molecules can be detected by using a double staining technique and analyzed by confocal fluorescence microscopy. In a preferred embodiment immunorecognition of the EGFR is performed by incubation with Ior egf/R3m mAb (5-20 µg/ml) for 1 hr, followed by an IgG antibody conjugated to rhodamine (Dako, Carpinteria, Calif., USA). In another preferred embodiment, NeuGcGM3 immunodetection is performed using biotinylated 14F7 mAb (5-20 µg/ml), 30 min. Followed by FITC-conjugated streptavidin (Dako, Carpinteria, Calif., USA).

The following examples illustrate a preferred embodiment of the present invention and therefore serve to illustrate it but in no case should they be considered as a limitation.

Figure 1:
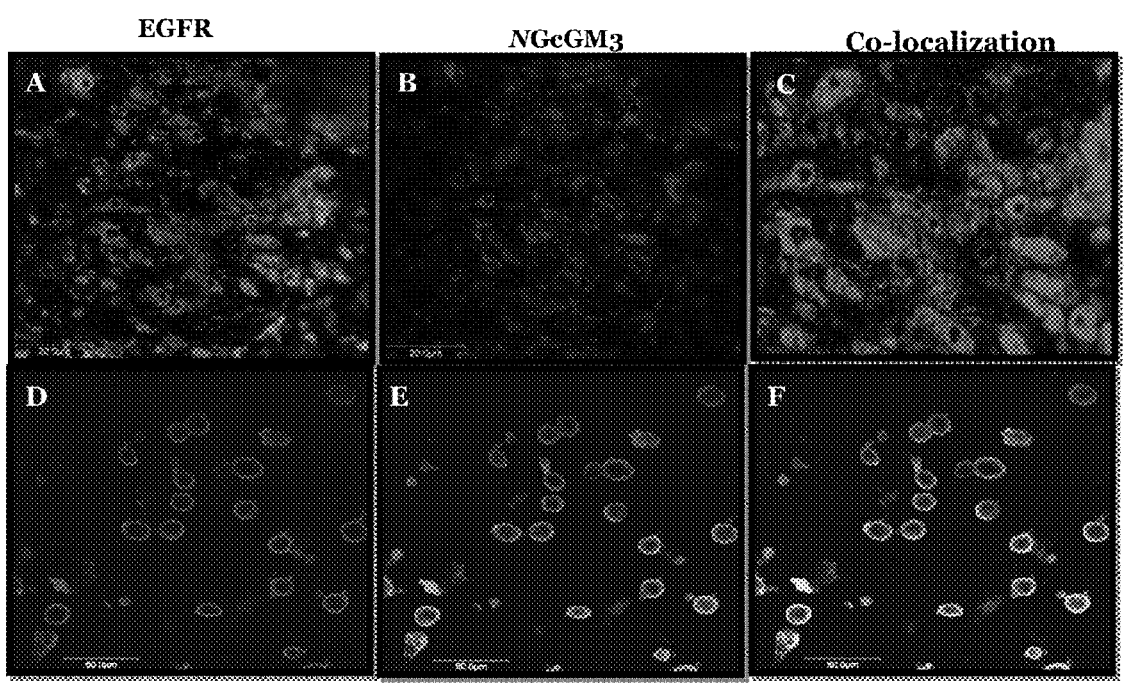
FIG. 1. The EGFR is co-localized with NeuGcGM3 ganglioside in different murine tumors. Co-localization (C and F) of EGFR and NeuGcGM3 ganglioside in the lung metastases induced in Lewis epidermoid carcinoma (A-C) and murine myeloma P3-X63-Ag.8653 (D-F).

VSSP) ganglioside vaccine therapies in a patient with retroperitoneal-peripancreatic hemangiopericytoma.

EXAMPLES

Example 1: Measuring EGFR and NeuGcGM3 Ganglioside Coexpression in Different Human Tumors The tumor samples were fixed in neutral buffered formalin and processed by paraffin inclusion technique, which is known to those skilled in the art.

The tissue sections obtained which had a thickness of 5 microns were maintained at 60° C. for 30 min, deparaffinized and rehydrated in a series of decreasing alcohols, kept in distilled water for 10 minutes and washed with TBS for 5 minutes. The reactivity of total tissue protein was blocked with a commercially available solution (Dako, Carpinteria, Calif., USA) for 30 min. The EGFR was immunodetected using the ior egf/R3m (20 µg/ml) for 1 hr. The immunorecognition of NeuGcGM3 was performed using 14F7 (MAb 20 µg/ml) for 30 min. After reaction of the primary antibodies, in both cases, the detection system used was Dako, LSABR Peroxidase System, DAB (Dako, Carpinteria, Calif., USA). Tissue sections were dehydrated and Mayers hematoxylin contrast was used (Dako, Carpinteria, Calif., USA). The negative control was obtained by substituting the primary antibody (Ior egf/R3m MAb or 14F7 MAb) by TBS wash solution (1×) and breast ductal carcinoma was used as a positive control.

The immunorecognition of the EGFR was located on the cytoplasmic membrane of tumor cells and the NeuGcGM3 ganglioside was detected intracytoplasmic and/or in the cytoplasmic membrane of cells.

Double staining: The EGFR was detected with Ior egf/R3m MAb (anti-EGFR) and then incubated with FITC-conjugated streptavidin (Dako, Carpinteria, Calif., USA). NeuGcGM3 was detected with biotinylated 14F7 MAb and subsequently with anti-murine IgG antibody conjugated to rhodamine (Dako, Carpinteria, Calif., USA). Co-expression of both molecules in tumor cells were identified in yellow in the images. Tissue sections were digitized and analyzed using a camera attached to an Olympus BX51 fluorescence microscope (Olympus, Japan). For the analysis of the digitized images ImageJ image processor version 1.43u was used.

Table 1 shows tumors from different localizations wherein EGFR and NeuGcGM3 ganglioside are co-expressed.

Intensity: −negative +weak ++moderate, +++intense.

| Histological types | EGFR | | NeuGcGM3 | | Double positive | |
|---|---|---|---|---|---|---|
| | Positive cases (%) | Intensity Range | Positive cases (%) | Intensity Range | Positive cases (%) | Intensity Range |
| Respiratory system | | | | | | |
| NSCLC | 8/10 (80) | ++/+++ | 6/10 (60) | +/+++ | 6/10 (60) | +/+++ |
| Digestive system | | | | | | |
| Stomach (ADC) | 3/3 (100) | ++/+++ | 2/3 (66.6) | ++/+++ | 2/3 66.6) | +/+++ |
| Colorectal (ADC) | 4/4 (100) | +/+++ | 4/4 100) | +/+++ | 4/4 (100) | ++ |
| Pancreas (ADC) | 3/4 (75) | ++/+++ | 2/4 (50) | ++/+++ | 2/4 (50) | ++ |
| Liver | 4/4 (100) | ++/+++ | 3/4 (75) | ++/+++ | 3/4 (75) | +/+++ |
| Urogenital system | | | | | | |
| Bladder | 2/2 (100) | ++/+++ | 1/2 (50) | ++ | 1/2 (50) | ++ |
| Nervous system | | | | | | |
| Glioblastoma multiforme | 5/5 (100) | +++ | 3/5 (60) | ++ | 3/5 (60) | ++ |
| Sarcomas | 2/3 (66.6) | +/++ | 1/3 (33.3) | + | 1/3 (33.3) | + |
| Haemopoietic system | | | | | | |
| Non-Hodgkin lymphoma | 2/3 (66.6) | + | 2/3 (66.6) | + | 2/3 (66.6) | + |

Example 2: Coexpression and Co-Localization Measurement of EGFR and NeuGcGM3 Ganglioside in Murine Tumor Models Murine tumor models used were Lewis lung carcinoma (3LL-D122), and Myeloma P3-X63-Ag8.653 (X63).

Double staining was performed to determine the co-expression/co-localization. The immunorecognition of EGFR was performed by incubation with 7A7 MAb (20 µg/ml), biotinylated, for 1 hr, followed by incubation with FITC-conjugated Streptavidin (Dako, Carpinteria, Calif., USA). Immunostaining of NeuGcGM3 was determined by incubation with 14F7 MAb (20 µg/ml), for 30 min, followed by incubation with an anti-murine IgG antibody conjugated to rhodamine (Dako, Carpinteria, Calif., USA). The negative control was obtained by replacing the primary antibody (7A7 MAb or 14F7 MAb) by TBS wash solution (1×). The co-expression was determined by using an Olympus BX51 fluorescence microscope (Olympus, Japan) and analysis of the digitized images using ImageJ image processor version 1.43u. The co-localization was determined by confocal laser microscope Flouview FV500 (Olympus, Japan). FIG. 1 shows the co-localization of EGFR and NeuGcGM3 in tumor samples from various murine models. The EGFR was identified with biotinylated 7A7 MAb followed by FITCcoupled streptavidin. The yellow color identifies the co-localization (C and F) of both molecules in tumor cells of murine models by color overlay.

Example 3: Measurement of Survival of C57BL/6 Mice Bearing Lewis Lung Carcinoma Treated with NeuGcGM3/VSSP Vaccine and 7A7 mAb Spontaneous Metastasis Model.

The animals were inoculated in the right footpad with $2\times10^5$ cells of Lewis epidermoid carcinoma (3LL-D122), in a volume of 0.05 ml, which corresponded to day 0 of the experimental protocol. On day 3 of the experiment the animals were randomized into four experimental groups of 10 animals each. On day 24, when the tumor reached a volume of 8-9 mm primary tumor surgery was performed. From day 48, observation of the clinical status of the animals began. Survival data were analyzed using the Log-rank test, $p<0.05$, and displayed on a Kaplan-Meier plot. The result includes three experiments performed on equal conditions.

Experimental Groups

Untreated Control. (T)

Passive anti-EGFR therapy: 7A7 MAb, intravenously at a dose of 56 µg in 200 µl of Saline Solution, on days 3, 5, 7, 9, 31, 33 and 35.

Active anti-NeuGcGM3 therapy: NeuGcGM3/VSSP vaccine, subcutaneously at a dose of 200 µg in 200 µl, on days 7, 21, 35 and 47.

Simultaneous administration of anti-EGFR and anti-NeuGcGM3 therapies as described for groups 2 and 3.

Figure 2:
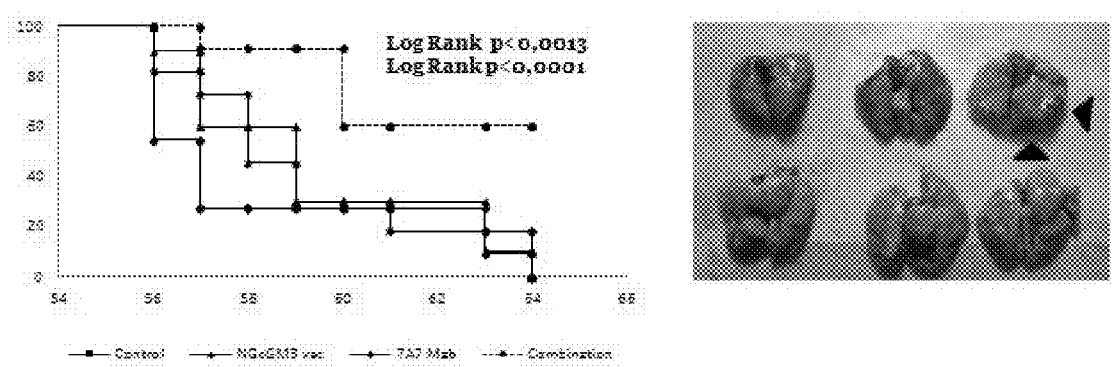
FIG. 2. Anti-EGFR therapy (7A7 MAb) in combination with NeuGcGM3 (NeuGcGM3/VSSP) anti-ganglioside vaccine synergistically increases the survival of C57BL/6 mice bearing Lewis lung carcinoma.

FIG. 2a shows that the simultaneous administration of anti-EGFR and anti-NeuGcGM3 (group 4) therapies on the lung metastasis model induced with Lewis lung carcinoma, increased survival of the animals by 60% compared with the other experimental groups. Surviving animals (one in group 4) were sacrificed one week after the end of the experiment and their lungs were removed. Macroscopic analysis showed that only one animal showed two lung metastases, noticing also that the rest the lungs of the animals were normal. (FIG. 2b). This result demonstrates a strong synergy of antitumor activity of anti-EGFR and anti-NeuGcGM3 therapies studied in this murine tumor model wherein EGFR and NeuGcGM3 are co-localized (see Example 2)

Example 4: Measurement of Survival of Cancer Patients Undergoing Therapy with Nimotuzumab Antibody and Racotumumab/Alumina Vaccine Given the finding on the frequent co-localization/co-expression of therapeutic targets EGFR and NeuGcGM3 ganglioside in samples of human lung tumor (Example 1); and the preclinical evidence shown in Example 3, we proceeded to study simultaneous treatment with anti-EGFR (Nimotuzumab antibody) and anti-ganglioside (Racotumumab/Alumina anti-idiotypic vaccine) therapies in lung cancer patients who had received the standard therapy for each tumor site and who had already disease progression.

Table 2 shows the test results from expanded use program (compassionate) of Racotumomab (1E10/Alumina) vaccine as single therapy or in combination with Nimotuzumab. Survival of cancer patients with non-small cell lung cancer (NSCLC) in advanced stages (Recurrent and/or Metastatic) is observed on it. It should be noted that patients on this study had received all established standard treatment lines and were only candidates for palliative, non onco-specific, therapy and that at the time of inclusion in the trial they had disease progression. In the group of patients that received therapy simultaneously against both targets a significant increase in overall survival at two years of treatment was observed, as compared with those who received only the monotherapies.

TABLE 2

Increased survival of patients with non-small cell lung cancer treated with anti-EGFR (Nimotuzumab antibody) and anti-ganglioside (Racotumumab/Alumina anti-idiotypic vaccine) therapies at two years of treatment.

| Treatment Groups | SV at 12 m (%) | SV at 24 m (%) |
| --- | --- | --- |
| Racotumumab/Alumina (n_86) | 42.7 | 16.1 |
| Nimotuzumab (n_165) | 36 | 21.4 |
| Racotumumab/Alumina + Nimotuzumab (n_88) | 40.7 | 37.7 |

Figure 3:
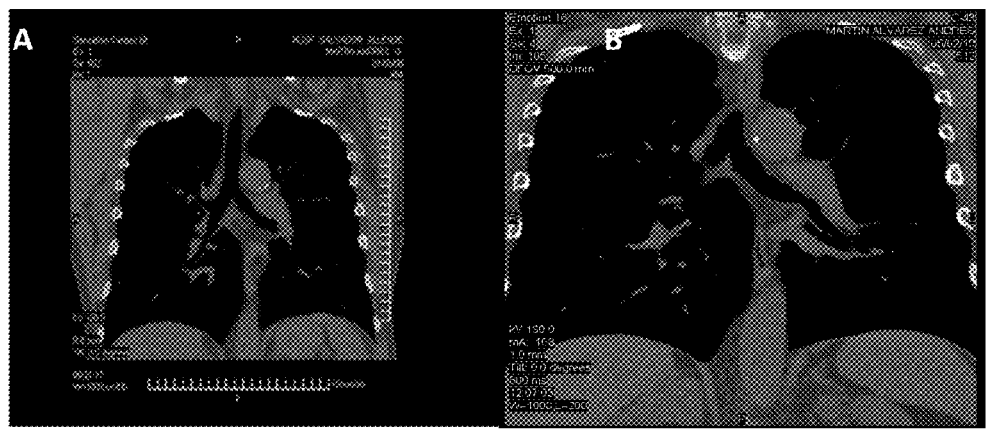
FIG. 3. Objective response to passive therapy against EGFR (Nimotuzumab) and NeuGcGM3 (Racotumumab/Alumina) anti-ganglioside vaccine in a patient with a non-small cell lung carcinoma.

FIG. 3 shows the objective response to passive therapy against EGFR (Nimotuzumab) and NeuGcGM3 anti-ganglioside vaccine (Racotumomab/Alumina) in a patient with NSCLC that, as mentioned above, had received all established standard treatments lines, which was candidate only for palliative, non onco-specific, therapy and that at the time of inclusion in the trial had disease progression. FIG. 3A shows the localization and extent of the tumor at the time of diagnosis. FIG. 3B shows the results from Computed Tomography (CT) at two years after treatment. In the latter figure only areas of fibroblastic response with areas of increased transparency in relation with bullae of emphysema that can be seen and no lung tumor lesion is observed. The same radiographic image remains three years later. This result indicates a surprising complete remission of a very advanced tumor as a result of therapy.

Figure 4:
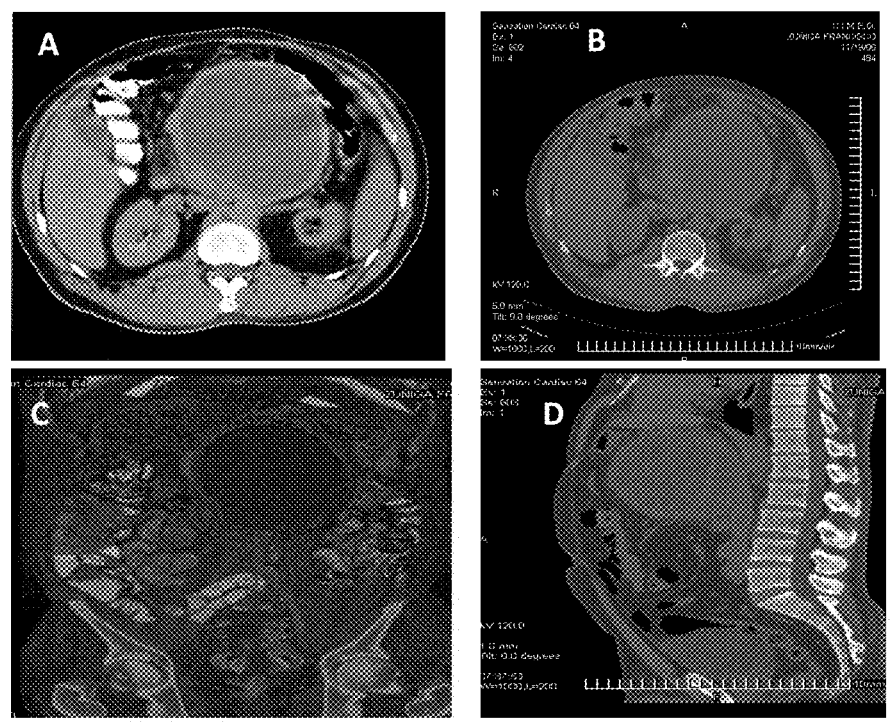
FIG. 4. Surprising clinical response to anti-EGFR (Nimotuzumab) in combination with NeuGcGM3 (NeuGcGM3/

Example 5: Measurement of Clinical Response in a Patient with Retroperitoneal-Peripancreatic Hemangiopericytoma Treated with the Nimotuzumab Antibody and NeuGcGM3/VSSP Vaccine FIG. 4 shows a sequential computed tomography of the abdomen of a patient with retroperitoneal-peripancreatic hemangiopericytoma (soft tissue tumor), with no response to radiotherapy and chemotherapy. The patient received anti-EGFR (Nimotuzumab) and anti-ganglioside (NeuGcGM3/VSSP vaccine) therapies 18 months after the initial diagnosis. The patient had severe pain and a throbbing tumor mass in the periumbilical region and weight loss of more than 15 kilos. FIGS. 4A and B correspond to the start time of therapies; C and D correspond to the evaluation after three years. Three years after application of treatment a stabilization of the disease can be observed, as evidenced by both images wherein the tumor size remains the same. Moreover, in the 72-month evaluation, patient maintains an excellent quality of life and is able to continue his working life. A tendency towards reduction of the tumor mass can also be seen. In summary, there is a surprising clinical benefit as response to the treatment.

Cancer patients treated with anti-EGFR and anti-ganglioside immunotherapy, as described in this invention, exhibit excellent tolerance (no significant toxicity) for long periods of treatment. The therapy promotes stabilization of the disease, increasing the quality of life, time to progression and overall survival of patients. The therapy described above has a superior effect to that observed in patients receiving traditional anti-EGFR or anti-ganglioside monotherapies.

The invention claimed is:

1. A method for retarding tumor growth of a tumor that co-expresses EGFR and N-glycolyl GM3 (NeuGcGM3) ganglioside targets in a patient in need thereof, comprising:
   (a) administering to a patient a medicament comprising a monoclonal antibody (MAb) directed against EGFR and,
   (b) administering to the same patient a medicament comprising a vaccine against NeuGcGM3 ganglioside.

2. The method according to claim 1, wherein
   (a) said MAb directed against EGFR is administered to said patient first and said vaccine against said NeuGcGM3 ganglioside is subsequently administered, or
   (b) said vaccine against said NeuGcGM3 ganglioside is administered to said patient first and said MAb against EGFR is subsequently administered.

3. The method according to claim 1, wherein said MAb directed against EGFR and said vaccine against said NeuGcGM3 ganglioside are administered simultaneously, staggered or alternately to said patient.

4. The method according to claim 1, wherein the vaccine against NeuGcGM3 ganglioside is NeuGcGM3/VSSP vaccine or anti-idiotypic Racotumumab/Alumina vaccine.

5. The method according to claim 1, wherein the dosage of the Mab is in the range from approximately 100 to 400 mg.

6. The method according to claim 4, wherein the dose of the NeuGcGM3 vaccine or the anti-idiotypic vaccine is in the range from approximately 0.1 to 2 mg.

7. The method according to claim 1, wherein said MAb is Nimotuzumab Mab.

8. The method according to claim 3, wherein said MAb and said vaccine against said NeuGcGM3 ganglioside are administered simultaneously in the form of a composition.

9. The method according to claim 1, wherein the vaccine has NeuGcGM3/VSSP as active principle.

10. The method according to claim 1, wherein the vaccine is Racotumumab anti-idiotypic vaccine adjuvated with alumina.

11. The method according to claim 1, wherein said patient is suffering from a tumor that co-expresses EGFR and NeuGcGM3 ganglioside targets.

12. The method according to claim 11, wherein said patient is suffering from a cancer selected from the group consisting of lung, breast, digestive system, urogenital system and sarcoma tumors derived from neuroectodermic tissue, and lymphoproliferative disorders.

13. The method according to claim 1, further comprising treating said patient with conventional radiotherapy.

14. The method according to claim 1, further comprising treating said patient with conventional chemotherapy.

15. The method according to claim 1, further comprising treating said patient with conventional radiotherapy and chemotherapy.

16. The method according to claim 1, wherein the patient experiences at least a 37% increase in survival percentage after 24 months of administration of the Mab directed against EGFR and the vaccine against NeuGcGM3.

17. The method according to claim 1, wherein there is less than 10% fall-off in survival of human cancer patients after 24 months of administration of the MAb against EGFR and the vaccine against NeuGcGM3 ganglioside compared to 12 months of administration of the MAb against EGFR and the vaccine against NeuGcGM3 ganglioside.

18. The method of claim 17, wherein the less than 10% fall-off in survival occurs in lung cancer patients.

* * * * *